US005684047A

United States Patent [19]

Butterfield

[11] Patent Number: 5,684,047
[45] Date of Patent: Nov. 4, 1997

[54] 4-GUANIDINOBUTYRAMIDE FOR IMPROVING BLOOD CIRCULATION

[75] Inventor: William John Hughes Butterfield, Cambridge, Great Britain

[73] Assignee: Cemorc Ltd, Cambridge, Great Britain

[21] Appl. No.: 448,546

[22] PCT Filed: Dec. 17, 1993

[86] PCT No.: PCT/GB93/02576

§ 371 Date: Jun. 16, 1995

§ 102(e) Date: Jun. 16, 1995

[87] PCT Pub. No.: WO94/13276

PCT Pub. Date: Jun. 23, 1994

[30] Foreign Application Priority Data

Dec. 17, 1992 [GB] United Kingdom .................... 9226313
Feb. 24, 1993 [GB] United Kingdom .................... 9303688

[51] Int. Cl.$^6$ ..................................... A61K 31/16
[52] U.S. Cl. ................................. 514/626; 514/866
[58] Field of Search ............................ 514/626, 866

[56] References Cited

PUBLICATIONS

Tinant et al., Hormone and Metabolic Research, 1(6), pp. 258–265, 1969.
Butterfield, Lancet, 342, pp. 533–536, 1993.

*Primary Examiner*—Kimberly Jordan
*Attorney, Agent, or Firm*—Saliwanchik, Lloyd & Saliwanchik

[57] ABSTRACT

The subject invention pertains to methods of using 4-guanidinobutyramide, or a physiologically-acceptable salt thereof, in a mammal or human to improve blood circulation.

6 Claims, No Drawings

4-GUANIDINOBUTYRAMIDE FOR IMPROVING BLOOD CIRCULATION

FIELD OF THE INVENTION

This invention relates to the regulation of blood flow in human patients. More particularly, it relates to the therapeutic use of a known compound in the prevention and/or treatment of complications associated with unsatisfactory circulation, e.g. of the type that are observed in diabetics, although the treatment is also suitable for non-diabetics.

BACKGROUND OF THE INVENTION

The compound 4-guanidinobutyramide (hereinafter "4GAB"), having the formula $HN=C(NH_2)-NH-(CH_2)_3-CONH_2$, is a naturally-occurring compound that is known for therapeutic purposes. GB-A-1195199 and GB-A-1195200 disclose 4GAB as a hypoglycaemic agent, the latter in combination with insulin, for the treatment of diabetes. In U.S. Pat. No. 3,639,628, 4GAB is shown to reduce abnormally high levels of blood urea in diabetics. It is also stated that "improvements of retinopathy and neuropathy have been observed"; it has now been shown that 4GAB has little or no effect on retinopathy, and indeed that it is not effective at the capillary level.

Aminoguanidine is a compound having a somewhat similar structure to 4GAB, which has been proposed for the prevention of diabetic complications. Aminoguanidine may suppress advanced glycosylation end-products, and has been reported to prevent the capillary lesions of retinopathy in diabetic rats.

SUMMARY OF THE INVENTION

According to the present invention, 4GAB or a physiologically-acceptable salt thereof, is used for the purposes of arteriolar dilatation. 4GAB is therefore useful in the regulation of blood flow, and in the prevention and/or management of complications that are observed, often in diabetics, in tissues such as the kidneys, nerves, skin and Islets of Langerhans. It may also have utility in treating male impotence (in diabetic cases, perhaps in cases of senile impotence, and more generally), by facilitating penile erection.

DESCRIPTION OF THE INVENTION

Without wishing to be bound by theory, it appears that 4GAB exerts its dilatatory effect through NO release through small vessels, arterioles. 4GAB is a compound in the metabolic sequence from the brain constituent GABA to arginine which itself is a precursor of NO. The metabolism of 4GAB to arginine is controlled by enzymes that may be glucose-related.

This mechanism explains the absence of effect on retinopathy and perhaps also the effects that have previously been associated with the administration of 4GAB. The mechanism and the results presented below show that 4GAB is of particular utility in treating or preventing renal complications, neuropathy and autonomic neuropathy (possibly by affecting neuronal nutrition) and providing improved circulation, e.g. in dementias or in counteracting the reduced circulation usually observed in old age.

In both diabetic and non-diabetic patients, 4GAB may act as an anti-neuropathic and, at least in some cases, as a protrophic agent. For example, it may reverse peripheral neuropathy and also incontinence associated with lack of suppression of urination. Infants lack control through a regular cycle of release, and a similar condition can develop in adult life and particularly in old age.

The possible mechanism and effects of 4GAB have been confirmed by the injection of radioactively-labelled 4GAB into mice. Radioautographs showed that almost all the injected 4GAB was immediately taken up in the walls of blood vessels. No specific localisation in any of the body organs concerned with glucose metabolism, e.g. the liver, kidneys and muscles, could be recognised.

4GAB can be produced simply and inexpensively. It is essentially non-toxic. It can be formulated with physiologically-acceptable carriers or excipients of any conventional type, depending on the mode of administration. Formulations, modes of administration and dosages are exemplified in GB-A-1195200 and U.S. Pat. No. 3,639,628, the contents of which are herein incorporated by reference.

The following Examples illustrate the utility of 4GAB.

EXAMPLE 1

A subject who was healthy but whose peripheral circulation was poor took tablets of 4GAB for a month. He reported a return of libido and penile erections, and that his feet were warmer to the touch.

EXAMPLE 2

Before treatment with 4GAB, a diabetic patient had a high fixed pulse rate. When he performed the Valsalva manoeuvre, it was obvious that he had lost the variations of pulse rate associated with slow deep breathing and forced breathing. This was presumably due to a specific diabetic autonomic neuropathic effect inhibiting the vagus nerve impulses to his cardiovascular system. An electrocardiogram of the patient showed the fast fixed pulse rate and, more importantly, a failure for any alteration of pulse rate as a result of deep breathing.

The patient was given 500 mg of 4GAB by mouth three times a day for two weeks. At the end of the treatment, his resting pulse had fallen from a fixed rate of 95 to just over 80 per minute and there were small variations in his pulse rate during deep breathing.

EXAMPLE 3

A group of 8 diabetics with fast resting pulses was tested. The pulses were monitored both at rest and during the Valsalva manoeuvre.

Administration of 4GAB was associated with a clear reduction in the resting pulse rate, which returned to earlier levels within 2–3 months of ceasing therapy. It was also observed that the patients were brought under control after 2–3 months by repeating the therapy. 7 of the 8 subjects showed an improvement in the sinus arrhythmia reflex, i.e. a return of pulse variation.

EXAMPLE 4

A patient whose diabetes had been treated over 30 years with insulin suffered from numbness in her feet. After 1–2 years of therapy with 4GAB, her requirement for insulin was reduced, and the patient reported sensations of feeling in her previously numb feet and also that sweating had returned in the skin of her lower legs. The administration of 4GAB did not prevent deterioration in her vision and the occurrence of retinal haemorrhages from her diabetic retinopathy. These observations are consistent with the theory that 4GAB affects the blood flow to the Islets of Langerhans.

EXAMPLE 5

A long-term diabetic patient was suffering from mild diabetic neuropathy, albumin urea and a succession of mild renal infections. Her treatment was augmented by the adminstration of 500 mg 4GAB per day, in tablet form. The 4GAB had a sparing effect on her insulin requirement. The clinical progress of her retinopathy was not affected, but the progress of her renal disease was, in contrast, remarkably slow. In the early stages of the augmented treatment, her glomerular filtration rate (GFR) was 28–30. 10 years later, her GFR was recorded as 40 (without any corresponding rise in blood urea levels).

I claim:

1. A method for improving blood circulation in a mammal or human patient in need of improved blood circulation which comprises administering to said patient an effective mount of 4-guanidinobutyramide, or a physiologically acceptable salt thereof, to improve said blood circulation.

2. The method, according to claim 1, wherein said mammal or human patient is suffering from complications associated with inadequate blood circulation in the kidneys, nerves, skin, or Islets of Langerhans.

3. The method, according to claim 1, wherein said human patient is in need of the prevention or treatment of male impotence.

4. The method, according to claim 1, wherein said mammal or human patient is diabetic.

5. The method, according to claim 4; wherein said human patient is treated with about 500 mg of 4-guanidinobutyramide per day in tablet form for a period of time sufficient to improve blood circulation.

6. The method, according to claim 1, wherein said 4-guanidinobutyramide, or a physiologically acceptable salt thereof, is administered with a physiologically acceptable carrier or excipient.

* * * * *

UNITED STATES PATENT AND TRADEMARK OFFICE
CERTIFICATE OF CORRECTION

PATENT NO. : 5,684,047
DATED : November 4, 1997
INVENTOR(S) : William John Hughes Butterfield It is certified that error appears in the above-identified patent and that said Letters Patent is hereby corrected as shown below:

Column 3, line 18: "mount of" should read --amount of--.

Column 4, line 10: "claim 4;" should read --claim 4,--.

Signed and Sealed this

Twenty-second Day of September, 1998

Attest:

BRUCE LEHMAN

Attesting Officer

Commissioner of Patents and Trademarks